(12) United States Patent
Marbach

(10) Patent No.: US 10,073,031 B2
(45) Date of Patent: Sep. 11, 2018

(54) OPTICAL ANALYZER, OPTICAL ANALYZING METHOD AND SAMPLE PREPARATION DEVICE

(71) Applicant: GrainSense Oy, Oulu (FI)

(72) Inventor: Ralf Marbach, Oulu (FI)

(73) Assignee: GrainSense Oy, Oulu (FI)

( * ) Notice: Subject to any disclaimer, the term of this patent is extended or adjusted under 35 U.S.C. 154(b) by 0 days.

(21) Appl. No.: 15/036,418

(22) PCT Filed: Nov. 14, 2013

(86) PCT No.: PCT/IB2013/060139
§ 371 (c)(1),
(2) Date: May 13, 2016

(87) PCT Pub. No.: WO2015/071706
PCT Pub. Date: May 21, 2015

(65) Prior Publication Data
US 2016/0299062 A1 Oct. 13, 2016

(51) Int. Cl.
*G01N 21/359* (2014.01)
*G01N 21/3563* (2014.01)
(Continued)

(52) U.S. Cl.
CPC ............ *G01N 21/359* (2013.01); *G01N 1/28* (2013.01); *G01N 21/3563* (2013.01); *G01N 21/59* (2013.01); *G01N 21/3554* (2013.01); *G01N 2201/0221* (2013.01); *G01N 2201/0632* (2013.01)

(58) Field of Classification Search
CPC .... G01N 21/359; G01N 1/28; G01N 21/3563; G01N 21/3554; G01N 2201/0221; G01N 2201/0632
See application file for complete search history.

(56) References Cited

U.S. PATENT DOCUMENTS 4,479,055 A 10/1984 Perten
4,540,286 A 9/1985 Satake et al.
(Continued)

FOREIGN PATENT DOCUMENTS

JP S6311841 A 1/1988
JP H02502490 A 8/1990
(Continued)

*Primary Examiner* — Christine S Kim
(74) *Attorney, Agent, or Firm* — Seppo Laine Oy

(57) ABSTRACT

Optical analyzer (10,50,60) comprises an optically integrating cavity (20), the optically integrating cavity (20) formed by at least one optical light diffusing wall (31) and adapted to contain a sample of a solid agricultural product, the sample consisting of one or more sample elements (41,48), a light source (13,33), emitting light into the optically integrating cavity (20), whereas the at least one optical light diffusing wall (31) is utilized to convert emitted light to diffused light, whereas the sample at least partially or completely converts the diffused light to spectrally filtered light, and a spectral sensor (26). The sample is confined in the optically integrating cavity (20) while the spectral sensor (26) is being exposed to the spectrally filtered light. Patent application has independent claims also for optical analyzing method and sample preparation device.

35 Claims, 4 Drawing Sheets

(51) Int. Cl.
   *G01N 1/28* (2006.01)
   *G01N 21/59* (2006.01)
   *G01N 21/3554* (2014.01)

(56) References Cited

U.S. PATENT DOCUMENTS

| | | | |
|---|---|---|---|
| 4,806,764 A * | 2/1989 | Satake | G01N 21/4738 250/339.07 |
| 5,256,886 A | 10/1993 | Wolf et al. | |
| 5,258,825 A * | 11/1993 | Reed | G01N 21/359 250/339.12 |
| 6,734,958 B1 * | 5/2004 | MacKinnon | G01M 11/00 250/228 |
| 7,087,901 B2 * | 8/2006 | Ambuel | G01N 21/3563 250/339.01 |
| 2005/0254053 A1 * | 11/2005 | Wright | G01N 15/1456 356/432 |
| 2007/0240242 A1 * | 10/2007 | Modiano | C12P 7/06 800/284 |
| 2013/0240754 A1 | 9/2013 | Iguchi | |

FOREIGN PATENT DOCUMENTS

| | | |
|---|---|---|
| JP | H04310848 A | 11/1992 |
| JP | H04310849 A | 11/1992 |
| JP | H04313049 A | 11/1992 |
| JP | H05288674 A | 11/1993 |
| JP | H07503533 A | 4/1995 |
| JP | H09311074 A | 12/1997 |
| JP | 4436886 B1 | 3/2010 |
| JP | 2010284736 A | 12/2010 |
| JP | 2012117817 A | 6/2012 |
| WO | WO8905465 A1 | 6/1989 |
| WO | WO9219958 A1 | 11/1992 |
| WO | WO 2012020440 A1 * | 2/2012 ............ G01N 21/31 |
| WO | WO2012020440 A1 | 2/2012 |

* cited by examiner

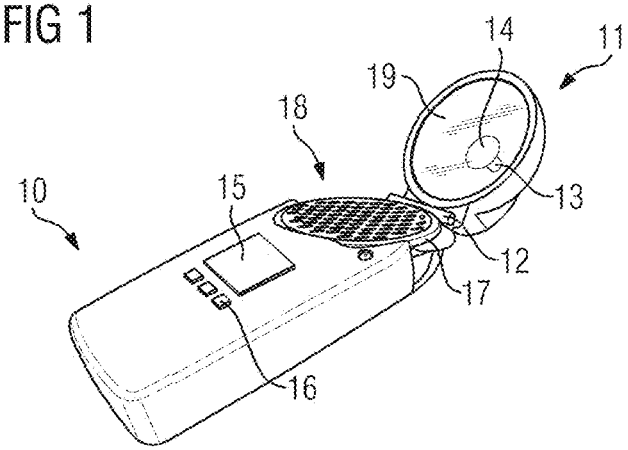
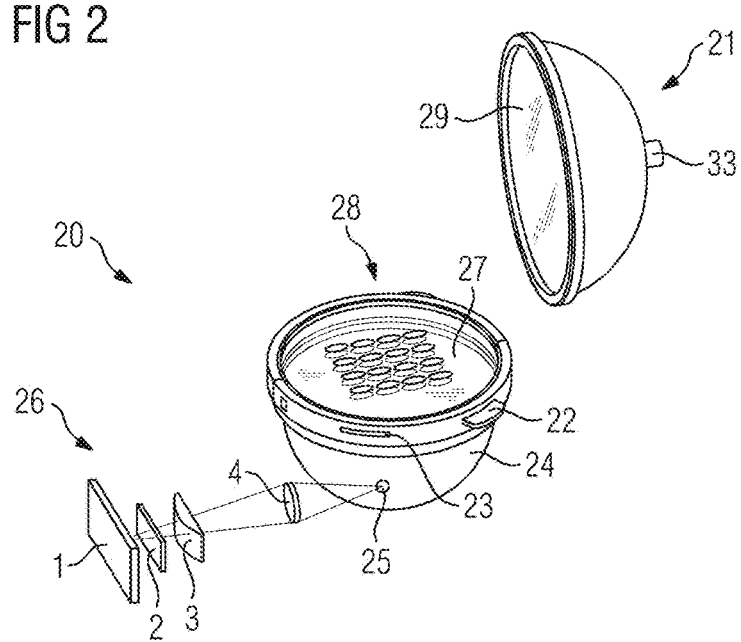

OPTICAL ANALYZER, OPTICAL ANALYZING METHOD AND SAMPLE PREPARATION DEVICE

FIELD OF INVENTION

The invention relates to an optical analyzer, in particular handheld analyzer, and corresponding method to analyze granular agricultural samples, such as grain, for contained substances whose concentrations are relevant for agricultural decision taking and planning, such as moisture or protein. Furthermore, the invention relates to a sample preparation device for conditioning agricultural samples for the optical analysis.

BACKGROUND OF INVENTION

From the prior art many methods are known to qualitatively or quantitatively investigate the ingredients of agricultural products, in particular grain. In order to figure out the value of a growing, harvested, or stored crop and to decide upon possible actions it is important to know about the ingredients.

Today, samples are taken and sent to specialized laboratories for analysis. Not available so far, however, except for moisture, are rugged and relatively low-cost analyzers for widespread use. The greatest demand is in the analysis of staple foods, i.e., crops that are routinely eaten by many people and that supply one or more of the three organic macronutrients needed for survival and health: carbohydrates, proteins, and fats.

Most staple foods are derived from cereals (for instance wheat, maize, rice) or root vegetables (for instance potato. Other staple foods include legumes (for instance beans or peas) and fruits (for instance apple, tomato, or nuts).

Low cost analyzers are available today only for moisture, where electrical properties of the sample can be measured (capacitance or resistance). In particular, moisture meters for grain are very common. One approach is to measure the change in capacitance of a capacitor into which a grain sample is placed. In U.S. Pat. No. 5,716,272 A the moisture content in grain is measured using this approach.

Optical methods can measure moisture more accurately and can also measure substances other than moisture, for instance, protein. Commonly, infrared light transmissive and reflective methods are utilized. In EP 0 511 184 A1 a reflective method is applied to a sample container with a window, whereas the window is used to obtain a reflective response from the randomly distributed sample elements.

U.S. Pat. No. 6,369,388 B2 discloses a handheld optical analyzer intended for various grains using a similar sample container, which can be placed into a light port for analysis taking into account the transmitted or the reflected near-infrared light (NIR light).

So far the evenly distributed, random deposition of the kernels in the grain sample was crucial in order to achieve a reliable transmitted or reflected response. For similar reasons also the approach of multiple light sources (NIR-LEDs) is used in U.S. Pat. No. 4,286,327 to be able to average over a number of light sources as well. However, the even and random distribution still remains a crucial premise for a reliable analysis.

Generally speaking, when measuring granular samples the transmissive methods bear the problem of accidental background noise originated in unfavorable sample element distributions, whereas the reflective methods bear the problem that only a minimum of the sample mass is taken into account. Most of the inner part of the sample remains hidden inside without having any effect on the spectral light filtering. This effect is not as problematic with transmissive methods, however, there a full absorption may take place due to the thickness of the sample resulting in nearly zero transmission or total absorption leaving no measurable signal.

The mass of the sample that does not contribute to the spectral filtering in one of the scenarios described above will be called "hidden mass" in the following. In many reflective measurements, the bulk of the sample mass is hidden due to the limited light penetration depth underneath the illuminated surface. In transmission measurements, even when performed at only moderate levels of overall absorption, large parts of the mass of a granular sample are often hidden by the fact that the majority of the detected light reaches the detector by sneaking through highly transmissive areas in the sample, such as the air gaps in a grain sample, rather than through the sample mass.

In WO 1999/40419 A1 a technique is disclosed where the sample preparation and preconditioning is optimized for the analysis. The optical analysis is performed on a continuous flow of harvested grain, whereas the analyzing beam is well-defined in space directed on an interaction area inside the sample flow. The optical setup is run in reflectance making sure that only the light with a sample interaction is taken into account. The reflected light contains mainly information on the ingredients in the superficial layer of the grain. The moving flow randomizes and therefore averages over the shape of the kernels and their positioning in respect to the light beam in a convenient way.

However, the problem remains to generate a reasonable randomization of the samples in order not to jeopardize the reliability of the spectrally filtered response. At the same time the optical analyzer itself should have an inexpensive, but reliable setup for measuring the concentration of the sample's ingredients and likewise an optical analyzing method should be easily feasible.

SUMMARY OF THE INVENTION

One aim of the invention is to not only rely on the optical filtering by granular agricultural samples that takes place in the outer layers of the sample or the sample elements, but also make the hidden mass available to the optical measurement in order to improve precision and reliability of the results.

Another aim of the invention is to reduce the amount of sample necessary to give a reliable measurement result.

Still another aim of the invention is to teach a handheld optical analyzer, which can be taken to agricultural production areas. Like this the waiting time and transportation of the samples taken can be eliminated.

Furthermore, another aim is to simplify the method being carried out in the agricultural production areas with a minimum of equipment and effort for sample preparation.

The invention has been driven by the insight that in previous optical methods the granularity of the sample was considered a nuisance. The desired state of the sample was uniform, and the methods relied on some form of averaging to overcome the effects of granularity.

The optical analyzer according to the invention comprises
an optically integrating cavity, the optically integrating cavity is formed by at least one optical light diffusing wall and adapted to contain a sample of a solid agricultural product, said sample consisting of one or more sample elements, a light source, emitting light into the optically integrating cavity, whereas the at least one optical light diffusing wall is utilized to convert emitted light to diffused light, whereas the sample at least partially or completely converts the diffused light to spectrally filtered light, and a spectral sensor, whereas the sample is confined in the optically integrating cavity while the spectral sensor is being exposed to the spectrally filtered light.

The sample is confined in the optically integrating cavity, which means that the sample is kept within the volume of the optically integrating cavity, where the optical integration takes place. The sample is hindered to leave said volume without necessarily being fixed or locked inside the cavity or fully surrounded or covered by it.

The photon density within the integrating cavity is nearly homogeneous. Therefore the diffused light is distributed well in the cavity and interacts with the sample either by reflecting or passing through the sample. In either case a spectral filtering of the diffused light takes place, which is characteristic for the ingredients contained in the sample. Ideally all or nearly all diffused light is converted into filtered light in order to achieve a good signal-to-noise ratio.

The sample is the object of the optical analysis. It contains or is made of a solid agricultural product. The sample may consist of one or more sample elements, for instance kernels of grain or smallest units of another solid agricultural product. The sample may just be a handful of hay or grass.

By definition, grain are small, hard, dry seeds harvested mostly for human food or animal feed and including cereal grains, pseudo cereal grains, grain legumes, and oil seeds. Selected parts of the harvested grain are used for next year's seed grain. A kernel is a single seed of grain.

Fodder or animal feed is defined as food carried by humans to feed domesticated livestock, as opposed to forage, which is material eaten directly by grazing livestock.

By definition, crop is the cultivated produce of the ground, growing or gathered. This definition includes any plant whose product is harvested by a human at some point.

Granular agricultural product (GAP) is any grain or other crop having a granular consistency, while growing or harvested and possibly processed. This definition includes root vegetables like potatoes; fruits like apples, berries, tomatoes, or nuts; fodder components like hay, silage, compound feed (pellets), straw, bran, or oilseed cakes; tobacco leaves; or forage components like freshly cut grass. This definition also includes the various lifecycle stages of the crop, for instance, in case of cereal grains like wheat or barley the kernels can be still growing or freshly harvested or dried or milled.

Granular agricultural products consist of physically separable smallest units. The smallest units will be called sample elements in the following. In case of whole grain, for instance, grain before milling, the sample elements are kernels. Kernels are similar unit-to-unit, albeit not necessarily uniform within-one-unit. In case of GAPs other than whole grain the nature of the sample elements may vary. The sample elements can be similar, for example, blue berries or pellets of compound feed (the latter are also uniform); or they can vary in physical size and shape, for instance, potatoes or straw. The sample elements of a hay or straw sample have varying elongated shape and can be chopped into yet smaller units, which then form the sample elements.

Advantageously, the sample of an agricultural product is not required to follow a flow or current, which would require a machinery to keep the flow running. It is not harmful to the spectral analysis if the sample elements, such as kernels in the case of a sample of whole grain or other sample elements in the case of a sample of other GAPs, are not entirely fixed at one place during the measurement. However, a fully static set of sample elements is easiest to realize, since the integration is not achieved by the sample elements moving around, but by the emitted light being diffused to interact with each sample element from nearly all sides. Experiments by the inventors have shown that the spectral characteristics of the filtered light in the integrating cavity, and therefore also the spectral results, are much more reproducible and reliable than in other methods. In fact, a sample contributes best to the spectral filtering of the emitted light when the sample elements are distributed inside the optically integrating cavity in respect to the other sample elements and the diffusing wall or diffusing walls in such a way that the diffused light can approach and interact with a majority or all sample elements from a maximum of directions.

Advantageously, there is very little shading of one sample element by neighboring sample elements. Some shading can be tolerated, but it may increase the hidden mass inside the optically integrating cavity.

Hidden mass is the share of the sample mass that does not contribute to the desired light filtering effect. As discussed above, the hidden mass effect can easily occur in granular samples since parts of the sample mass tend to effectively shield other parts from the measurement light. Inside an integrating cavity, hidden mass effect is caused by within-sample shading and can be minimized or even eliminated by locating the sample's individual sample elements at a minimum distance from each other, so that all units are illuminated from a maximum of directions. A second type of hidden mass effect can occur within a single kernel or other sample element. This happens when the absorption coefficient(s) at the used measurement wavelength(s) is(are) so large in relation to the physical size of the sample element that the photon density inside a given sample element is greatly reduced compared to the photon density impinging on its surface.

Keeping a minimum distance between neighboring sample elements helps to further reduce the second type of hidden mass effect.

The optically integrating cavity further circumvents the problem of direct sensor light exposure, because the emitting light is diffused by the light diffusing wall or alternatively or additionally by a baffle, which takes care that the emitting light becomes diffuse probing light by homogeneously distributing the emitted light into nearly all directions.

The spectral sensor has the function to capture at least a part of the filtered light by exposing the sensor to the light coming from the optically integrating cavity, which contains filtered diffuse light and may also contain unfiltered diffuse light. Because the measurement time resolutions in question are much longer than 1 nanosecond, the contributions are very effectively mixed and the light output to the sensor is a very stable mix (1 ns is equivalent to about 1 foot of light travel). This situation is by far not as problematic as the uncontrollable direct throughput of emitted light in a transmissive optical analysis. In case of the optical cavity, unfiltered diffuse light simply generates an offset in the sensor signal, which over the relevant spectral range reproduces the spectrum of the used light source. Hence the filtered diffuse light can be easily separated from the unfiltered diffuse light.

The optical filtering of the sample depends on the type and amount of contained substances and on their absorption coefficients. The filtered light has an absorption spectrum, which is a mathematical superposition of all absorption spectra of the ingredients inside the sample, whereas each ingredient's absorption spectrum is scaled by a concentration parameter. Therefore the analysis may include a regression, in particular a linear regression, of the characteristic absorption spectra of the known contained substances and ingredients, such as oil, moisture, protein et cetera, whereas each absorption spectrum is multiplied by the corresponding concentration parameter. Hence the obtained absorption spectrum of the filtered light can be fitted by choosing the correct concentration parameters. This approach is possible, because the concentrations of the ingredients are directly proportional to the amplitude of the characteristic absorption peaks. Alternatively, so-called inverse regression methods like PLS or PCR can be applied, which regress a number of measured spectra against their actual analyte concentrations as determined by a reference method and then use the solution to predict new spectra.

Advantageously, at least some or all of the sample elements are suspended separately from each other within the optically integrating cavity. Like this a nearly all around diffuse illumination with the emitting light is possible, in order to avoid unnecessary hidden mass. In particular, the sample elements are advantageously brought into position by a guiding assisted sample opening, which converts the kinetic energy of the filling process into a systematic non-shading distribution. Such guiding assistance may partly or fully consist of a funnel, a nozzle or any kind of guiding slope to place the sample elements in a favorable distribution.

Even better would be an optical analyzer that is adapted to allocate the sample elements at a minimum distance from each other. Like this the shading is also prevented. This might be combined with an also defined distance from the closest diffusing wall of the integrating cavity.

Advantageously, the optical analyzer is adapted to analyze an optically thin sample. A sample is optically thin if the hidden mass effect is below approximately 40%. Nearly ideal measurement conditions can be found at hidden mass values of less than about 10%.

Fortunately and so far unrecognized, many important types of grain, including wheat and barley, can achieve this ideal sampling situation relatively easily because, when measured in the third overtone NIR wavelength range, their kernels are small enough to be optically thin individually. By arranging these kernels with a minimum distance to each other inside the optically integrating cavity, the whole sample becomes optically thin. For example, when measuring barley kernels in this way the hidden mass for optical wavelengths near 1000 nm is only approximately 13% even for relatively large kernels of approximately 53 mg weight. The hidden mass of wheat kernels is typically less than 10%, the kernels having around 40 mg of weight. Last not least, rice, having a kernel weight of between 19 to 25 mg, has hidden mass of only about 5%.

The sample elements of other granular agricultural products, on the other hand, such as maize or apples, need to be chopped or squeezed or otherwise reduced in size in order to generate an optically thin sample. In the third overtone NIR wavelength range, many GAP materials become optically thin once the geometrical thickness of the sliced or pressed material plate is thinner than about 3 millimeters. The thin-plate geometry achieves optical thinness in one dimension, which is sufficient to achieve thinness of the whole sample. Once a sample is arranged in an optically thin way, its mass acts as a predominantly transparent sample for the diffused light inside the integrating cavity. For very small sample elements, such as the kernels of flax, even several layers on top of each other still generate an optically thin sample, since the light passes through a multiple of these sample elements with small attenuation only.

The hidden mass of a given sample can be measured using a simple experiment. First, the absorbance signal of the sample is recorded in the original state of the sample. Second, the sample elements are separated from each other (assuming this is not already done) and re-measured inside the integrating cavity. Comparing the amplitudes of the two absorbance spectra determines the hidden mass effect due to element shading that affected the original sample. Finally, by chopping the sample elements into smaller and smaller pieces and re-measuring the separated pieces in the integrating cavity, the full extent of the hidden mass effect can be determined. With each chopping the hidden mass is reduced until the pieces are so small to only act as a transmissive filter. In this state the hidden mass is 0% and the probed mass is 100%. In the 800 to 1050 nm wavelength range, the asymptotic reduction is very quick in practice. For example, if large barley kernels weighing around 53 mg are used as sample elements, they only require one length-wise cut to nearly eliminate the (already negligibly small) hidden mass effect shown by the whole kernels.

Advantageously, the solid agricultural product is a granular agricultural product (GAP), such as grain, in particular wheat, barley, maize, barley, oats, rye, or members of the pea family, such as beans, or fruits, such as apples, blue berries, or pellets of compound, such as pellets of feed or straw compound.

It makes sense to distinguish between grain samples and other samples because many types of grain have kernels small enough to be individually optically thin. Hence their samples can easily be arranged into optically thin samples. Many of the other samples like potatoes or apples or straw or oilseed press cakes, need some form of manual or mechanical preprocessing in order to generate a representative, optically thin sample.

Furthermore it is advantageous if the optical analyzer has an energy storage capable of storing an energy load sufficient for the optical analyzer to carry out a spectral analysis of the sample. Like this the optical analyzer is a mobile analyzer and does not depend on any electricity power connection to a electricity network, which allows the user to set the analyzer to work far away from any electricity supply system, for example, on a corn field far away from any inhabited area. Particularly advantageous as an energy storage is a storage of electric energy, such as a battery or rechargeable battery.

The usage of the optical analyzer is improved if it is adapted to carry out an optical analysis of the sample while being held manually, in particular, held by a human hand or held by only one human hand. Like this the optical analyzer can be handled very easily and can be operated at any test site, even if there is only one testing person present. The single testing person is then capable of getting the sample from the crop, precondition it, if necessary, and put it into the optical analyzer. After that the optical analysis can be initiated and carried out. The concentration results are readily available.

Advantageously, the space between the sample elements is kept non-absorbing or nearly non-absorbing in comparison to the absorption of the sample elements making up the sample. Like this shading of the sample elements within the sample can be avoided and the hidden mass be kept low. In case there is a holding apparatus for the sample, such as a sample holder, the apparatus should consist of a material being transparent for the emitted light. Ideally the space between the sample elements is completely non-absorbing, for instance, occupied only by air.

If the sample elements are very small, like for example in the case of flaxseed, it is possible to simply pour a multiple of sample elements into an indentation or dip of the sample holder, whereas the volume of the indentation or dip supports the optical thinness in at least one direction. A tool may be used to remove sample elements exceeding the volume of the indentation or dip of the sample holder.

In order to further reduce the hidden mass effect favorably some or all of the sample elements are advantageously allocated in a plane, a line or a sphere to allow a homogeneous illumination of the sample from nearly all spatial directions. For the analysis it is optimal to distribute the sample elements, such as kernels, uniformly over the whole space inside the optically integrating cavity, because then there is maximum possible distance between the sample elements. However, for reasons of practicability two-dimensional distributions may be favored.

In another preferred embodiment the sample is a sample plate cut from a single sample element of the crop, for instance, from a single potato or apple. By cutting the sample to form a plate it ideally fulfills in the normal direction the criteria of optical thinness, in particular when having a thickness of less than about 3 millimeters. Advantageously, no sample holder is required, since the cut or pressed sample plate can be placed inside the optically integrating cavity maintaining itself therein. Alternatively the sample plate consists of a multiple of cut or crushed sample elements, e.g. beans or maize kernels or a multiple of pressed sample elements, e.g. hay or straw.

If the sample elements are allocated by indentations of a sample holder and the optical analyzer is adapted to receive the sample holder in the optically integrating cavity, the usage of the analyzer is greatly simplified, because the sample holder takes care of the positioning of the sample elements and also the number of the sample elements measured can be kept nearly equal for every analysis. Also the optically integrating cavity is protected since it does not need to be opened and the diffuse walls are not exposed to the outside, which helps to avoid staining of the diffusing wall surface. Said indentations may consist of clearings or holes in the sample holder or alternatively the indentations are implemented as hutches or recesses.

Advantageously the sample holder is in part or completely transparent for the emitted light, unless the sample holder forms a part of a light diffusing wall of the optically integrating cavity, which may help to properly close the optically integrating cavity around the sample holder and prevent daylight from coming into the optically integrating cavity. Also, a sample holder is advantageous if it can be cleaned easily so that no dirt and particles are present on the sample holder, when the sample holder is located inside the optically integrating cavity during a measurement.

Advantageously, the sample holder has between 50 to 110 indentations, in particular 70 to 80 or 100 indentations, each indentation adapted to position or hold a sample element. Like this the quantity of sample is clearly reduced in comparison to optical analyzers of the prior art. This is true, in particular, if the sample elements are individually optically thin, as in the case of wheat or barley, so that the total hidden mass is negligible and virtually all of the sample mass is probed and participates in the generation of the spectrally filtered light. In the grain trade, appropriate indentation shapes are known that facilitate manual loading, meaning, the indentations fill easily with one and only one kernel each. Optimized shapes vary between different types of grain and, to a lesser extent, also between different cultivars of the same type of grain. The sample holder is advantageously adapted to be easily removed and re-inserted into the analyzer so that the user can easily exchange one sample holder for another in order to measure a different type of grain.

Advantageously, a thickness of the sample holder corresponds to the characteristic thickness of an optically thin sample, in particular, the characteristic thickness of approximately 2 to 4 millimeters or less than approximately 4 millimeters. Like this the sample holder can be filled with a sample not fulfilling the hidden mass criterion and can be used as a guiding element to properly resize the kernels or other sample elements for a lower hidden mass and even optical thinness. The thickness of 2 to 4 millimeters fulfills the requirement of optical thinness for most grains.

In a preferred embodiment, the sample holder is placeable and/or is fixed inside the optically integrating cavity by means of a frame, by means of a form fit or by means of a force closure. Like this the position of every sample element within the optically integrating cavity is well defined in respect to the diffusing wall or the diffusing walls of the optically integrating cavity, which further helps the reproducibility of the spectral results. Either the cavity can be opened to introduce the sample elements or a sample holder is adapted to be placed and fixed inside the optically integrating cavity. A frame is advantageous, because it may serve as a handle on the sample holder and/or the frame might be used to close or lock said cavity.

Advantageously, the optical analyzer has a sample slot for inserting the sample or sample holder. The sample slot serves to properly place the sample or sample holder inside the optically integrating cavity by manual loading or automated feeding. The frame or other closure may serve additionally or alternatively to prevent daylight or other disturbing light to get into the optically integrating cavity.

In a favorable embodiment a blade or a pair of blades is positioned at an entrance opening of the slot to convert a sample to an optically thin sample by partial slicing when the sample is inserted into the optical analyzer. Like this the preparation of the sample and inserting it into the optical analyzer is combined to one preparatory step before the measurement.

In a preferred embodiment the optical analyzer is enabled to perform spectral analysis on several different types of granular agricultural product. This is especially possible if the analyzer is designed to measure agricultural products of physically similar type, for instance, small grains like wheat and barley; or larger grains like maize and fava beans; or hay and straw; or powders like flour; or fruits and roots that need to be cut into a single plate like apples and potatoes. In this way, the products are classified according to the pretreatment necessary to transform them into representative samples with minimum hidden mass. After the pretreatment they can be introduced as samples into the optical analyzer.

Advantageously, the sample is a treated granular agricultural product, particularly a chopped, sliced or crushed granular agricultural product. Like this the hidden mass can be reduced and the filtering share of the sample mass increases. Ideally, the treatment leads to optical thinness of the sample.

Preferably, the light source is a light bulb, light emitting diode (LED), a broad bandwidth emitting diode, a halogen lamp or a multiple of said light sources. In order to detect absorption bands of the ingredients, whose concentration is to be measured, it is advantageous to use an emitted light, which is at least close to be spectrally continuous, such as thermic light sources. Also a multiple of LEDs might be used as a light source to cover the required wavelength spectrum. The spectral analysis is not disturbed by a characteristic structure of the spectrum of the emitted light.

Advantageously, the wavelength spectrum of the light source is at least partially located in the spectral range from 800 to 1050 nanometers. The light source produces the emitting light, which contains a spectral wavelength range that ideally includes the near infrared $3^{rd}$ overtone region ($3^{rd}$ harmonic) from about 800 to 1050 nanometers. This region covers characteristic absorption bands of the most important ingredients of granular agricultural products, such as moisture, lipids, protein et cetera, and silicium (SI) detectors are still capable of detecting this wavelength range.

In order to achieve a homogeneous diffusion of the emitted light in the volume of the optically integrating cavity, preferably the optical light diffusing wall is painted with a diffuse white paint, the optical light diffusing wall has a layer of highly diffuse material or the optical light diffusing wall is made from a diffuse material. The effect of diffusion causes the emitted light to generate diffused light by bouncing on the diffusing walls or on at least one of the diffusing walls of the optically integrating cavity and thereby randomly distribute light irradiance into multiple directions within the optically integrating cavity, which constitutes the diffused light. The surface of the light diffusing walls ideally is white over the wavelength range of the measurement and has diffuse reflection of better than 95%. This might be achieved in various ways. Firstly, a diffuse white paint, such as Duraflect™ might be applied to the cavity walls. Secondly, a layer of highly diffuse material might be applied on the cavity walls, for example ODM98-F01. Thirdly the cavity walls might be produced from a suitably white material, such as Spectralon™ or polyethylene containing a high pigment-volume-concentration of $TiO_2$ particles. Additionally the polyethylene might be easily injection-molded to form the optically integrating cavity in part or fully.

In a preferred embodiment the optically integrating cavity mainly consists of two half-spheres. Like this the advantages of a so called Ulbricht sphere can be put forward. Interestingly, the sample holder may be placed between the two half-spheres for the measurement. Moreover, the optically integrating cavity has the form of a sphere, which per se leads to advantageous diffusion characteristics.

Also at least one of the half-spheres is preferably sealed with a transparent protection, particularly a protection glass. The protection glass prevents dirt and other disturbing substances and also the sample itself to interact with the cavity walls. Hence, the diffusion ability of the diffusing walls is not affected.

Advantageously, the spectral sensor has a detector array, a linear variable optical filter and/or focusing means. The detector array can be used in case the single detectors of the array can be assigned a certain wavelength or wavelength range, which can be achieved by a spectrally diffracting element, such as a prism or grating. Like this no scanning arrangement needs to be used, which requires movable optical elements. Similarly a variable optical filter may be used in a similar fashion. The focusing means are basically lenses or elements having a focal length to act on the beam with.

Preferably, an analysis of an absorption spectrum provided by the spectral sensor results in the concentration of protein, moisture, carbohydrate and/or oil contained within the sample. Also any other concentrations or property values may be found by the optical analysis, which are useful for agricultural decision taking and planning. Ideally, the optical analyzer is adapted to analyze the concentrations of a number of ingredients sequentially or simultaneously.

Another preferred embodiment has computer software, which enables the computer to at least carry out the analysis of the spectrally filtered light by generating the absorption spectrum of the sample. Additionally, any other step of the following method may be aided or controlled by said software.

The optical analyzing method according to the invention has the steps:
  emitting optical light into an optically integrating cavity, whereas at least one optical light diffusing wall of the optically integrating cavity converts emitted light to diffused light and
  at least partially or completely converts the diffused light into spectrally filtered light by utilizing a sample of a solid agricultural product, the sample being confined in the optically integrating cavity while the spectral sensor is being exposed to the spectrally filtered light, and
  analyzing the spectrally filtered light by generating an absorption spectrum of the sample.

The optically integrating cavity leads to a simplification of the method that allows a local and fast analysis of a sample of a granular agricultural product. Also, said sample does not need much preparation for the analysis, if there needs to be a conditioning at all.

If the diffusing wall is not sufficient for the required degree of optical integration as it is done in a so called Ulbricht sphere, then more diffusing walls or baffles may be added, whereas both generate diffused light by reflection.

Advantageously, a quantitative analysis is carried out by generating an absorption spectrum of the sample, whereas its amplitude is proportional to the absorption coefficient of the sample inside the cavity. The absorption spectrum is generated by measuring a reference spectrum of the unloaded integrating cavity with no sample present and by comparing the sample spectrum of the loaded cavity with the reference spectrum. Like this all spectral filtering effects of the optically integrating cavity or a sample holder can be taken into account when analyzing the filtering action of the sample. Some of the filtering action does not originate from the sample, which might happen, when having a dirty sample holder or a dirty optically integrating cavity. Advantageously, the user does not need to clean the optical analyzer thoroughly or even not at all, since the effects of the dirt can be eliminated from the spectral analysis.

For calibration purposes a dark spectrum is measured while the light source is switched off or shuttered. This takes care of any side effects acting on the sensor, which have no relation to the optical analysis of the sample and might be attributed to a characteristic sensor response. The dark spectrum can be re-measured at predetermined time intervals, for instance, immediately before and after the sample and reference spectra are measured. The sample and reference spectra can then be dark-corrected before computing the absorption spectrum from the two. The amplitude of the absorbance spectrum is then even better linear in the concentrations of the sample ingredients.

In a preferred embodiment the sample elements are allocated in the optically integrating cavity at a minimum distance from each other to prevent shading and help reduce the hidden mass to approximately 40% and ideally to less than approximately 10% of the total sample mass.

Advantageously, an optically thin sample is analyzed, particularly an optically thin sample with a thickness in one dimension of approximately 2 to 4 millimeters or less.

Optical thinness is not always required if the precision of the concentration results does not need to be very good.

A useful embodiment of the method includes a spectral analysis carried out by an optical analyzer powered by an energy storage capable of storing an energy load sufficient to carry out a spectral analysis of the sample. Like this the user is able to perform optical analyses far away from private or public power supply networks. Advantageously, the energy storage is a storage of electric energy, such as a battery or a rechargeable battery.

A sample preparation device according to the invention has a sample holder having a multiple of indentations and a first movable blade, the first blade being movable in a first plane, which is defined by a first set of openings of the indentations. Said device is very useful since the sample holder can be used for the sample preparation as well as for the optical analysis in the optical analyzer.

Preferably the optical analyzer has a second movable blade, the second blade being movable in a second plane parallel to the first plane and being defined by a second set of openings of the indentations. Thereby the sample elements are sliceable in whatever slicing thickness, ideally a thickness that qualifies for optically thinness, and are squeezed into the indentations in such a way that they are stuck in the indentations not requiring any more fixing means during the measurement but still can be reasonably simply removed afterwards.

Advantageously the first blade is fixed to the second blade in such a way that both blades at least partially slice a sample allocated in one of the indentations simultaneously to ensure selected sample thinness with greater precision.

Ideally a shortest distance between the first and second blade corresponds to a characteristic thickness for a particular type of sample that makes the sample optically thin, in particular, with a characteristic thickness of about 2 to 4 millimeters or less. Such apparatus is useful for maize in particular.

In another embodiment the sample preparation device consists of three layers of glass, whereas the middle one moves and thereby cuts the sample elements into three slices. Then the sample is optically thin, but still consists of the whole mass of the kernels producing less sampling error.

Other favorable embodiments and advantageous implementations of the invention are described in the drawings or the dependent claims.

BRIEF DESCRIPTION OF THE DRAWINGS

In the following, the invention is explained in more detail with reference to the examples shown in the attached drawings in FIG. 1 to 7, of which:

FIG. 1 shows a handheld optical analyzer with an optically integrating cavity based on two half-spheres, FIG. 2 shows a schematic setup of an optical analyzer with an open optically integrating cavity.

Same reference numerals refer to same components in all FIG.

DETAILED DESCRIPTION OF PREFERRED EMBODIMENTS

Figure 3:
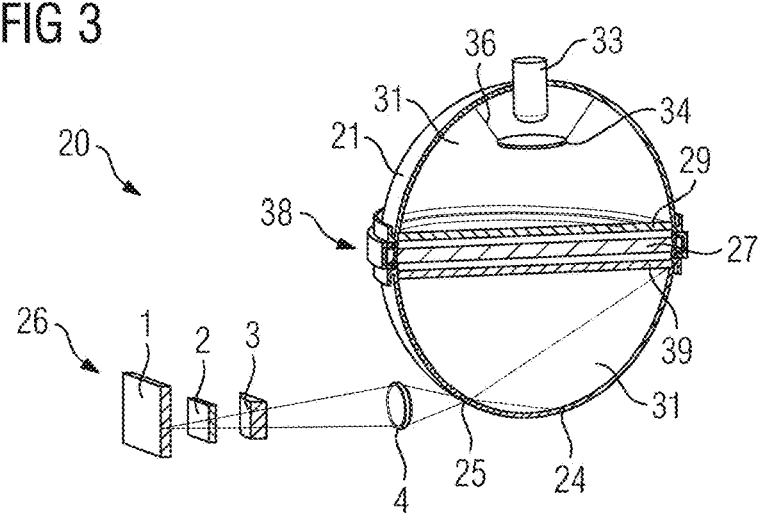
FIG. 3 shows the schematic setup of FIG. 2 in cross-section with the optically integrating cavity closed, FIGS. 4A, B show the sample preparation with a sample preparation device.

FIG. 1 shows a handheld optical analyzer 10 with an optically integrating cavity based on two half-spheres 11, whereas the half-sphere 11 is connected to the optical analyzer 10 using a hinge 12. The sample holder 17 is integrated into the housing of the optical analyzer 10. The second half-sphere below the sample holder 17 (not visible) is also integrated into the optical analyzer 10 without user access to avoid contamination. The sphere has an inside diameter of 80 millimeters.

Alternatively the sample holder 17 may be removable to allow collecting samples directly into the holder 17 by inserting it into a heap of sample elements and then place it inside the sphere.

The sample elements, for example, kernels of a certain grain are spread into the indentations 18. At least about 80% of them should be filled in order to generate an acceptable signal-to-noise ratio. Ideally there are indentations 18 for about 80 sample elements. The sphere might be filled by putting the samples elements into the sphere and shaking or moving the sphere in an open or closed state.

After the filling, lid 11 is closed to seal the optically integrating sphere during the measurement. The baffle 14 ensures that no emitted light from light source 13 is directly transmitted to the sample elements. The light source 13 is a low cost, low power halogen lamp with a nominal voltage of 12 Volts. This way battery operation is possible.

The protection glass 19 avoids the pollution of the movable half-sphere 11. Also, the protection glass 19 is flat and therefore easily cleanable. The same applies for the sample holder 17, whose preferred material is a borosilicate glass and can be washed with standard cleaning equipment without affecting its transparency for the diffused light.

The user closes the lid 11 and starts the measurement by pressing a button 16. A few seconds later the concentration of protein and moisture are shown on the display 15 in units of [% w], if previously a reference spectrum was taken without any sample in the sample holder 17. Like this a quantitative analysis is carried out quickly and reliably.

Typical concentrations of grains are roughly 10% of protein, 5 to 15% of moisture, 70% of carbohydrates, 4% of fat and 2% of minerals alias ash in a dried state.

The optical analyzer 10 is lightweight, portable and can be operated manually by a single person. It is powered by a set of standard batteries, which can be recharged by connecting the optical analyzer 10 to a solar charging device (not visible).

Preferably the optical analyzer should be able to communicate wirelessly with other wireless (WLAN, Bluetooth™) devices such as a mobile phone or a mobile computer to transfer the measurement results for further processing. Alternatively, a universal serial bus (USB) connection might be deployed.

FIGS. 2 and 3 show a schematic setup of an optical analyzer with an optically integrating cavity being formed by two half-spheres 21,24, which can be connected to each other using a bayonet closure, for example. Optionally the sample holder 27 can be fixed to the housing (not shown) or the upper sphere 21 using the slot 23. In FIG. 2 the optically integrating cavity is opened and in FIG. 3 it is closed using a frame 38, which establishes a form fit to at least one of the half-spheres 21,24. The frame 38 can be made of plastic or metal materials as long as their diffuse reflection is high enough not to hamper the integration ability of the optically integrating cavity 20, which is formed by half-spheres 21,24 and part of the inner surface of frame 38.

Like in FIG. 1 the protection glass 29 is used to protect the inner part of the upper half-sphere 21 including the front part of the light source 33, which sticks out of the half-sphere to be easily replaceable, since the protection glass 29 is not removable.

The indentations 18, 28 (in FIG. 1 as well as in FIG. 2) are defined by a volume that allows the placement of a single kernel of wheat as sample elements. Any placed kernel blocks the occupied indentation 18,28 for any further kernel, which simplifies the distribution during loading.

The spectral sensor 26 could also be replaced by other spectrographic sensors. Through the opening 25 in the lower half-sphere 24 some diffused light and filtered, diffused light is directed by some beam guiding elements, such as lenses 3,4 to a linear variable bandpass filter 2 and finally to a detector array 1. Every pixel of the detector array, preferably with a row of 64 pixels, corresponds to a certain wavelength of interest whereas the filter takes care of transmitting the correct wavelength onto the corresponding pixel. The linear variable optical filter may also be replaced by a grating or a prism.

The sample holder 27 is not fixed inside the sphere 20, which may also be called an Ulbricht sphere 20. The sample holder 27 might be filled inside or alternatively might be taken out for said purpose. Hence there is a second protection glass 39 to also protect the white diffusing wall 31 of the half-sphere 24 for optimal light homogenization. Furthermore the frame 38 may be designed to hold the sample holder 27 tightly together with both half-spheres 21,24. Advantageously, frame 38 is permanently connected to sample holder 27.

Figure 4A:
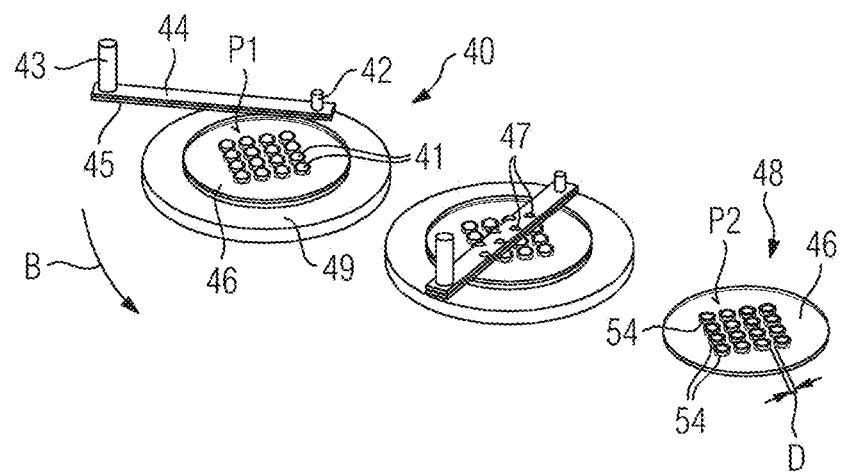
Figure 4B:
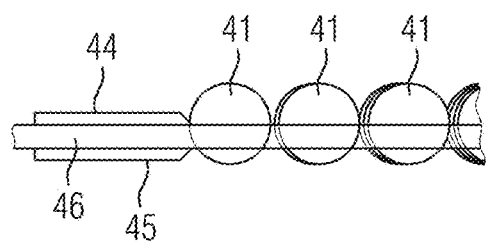

FIGS. 4A, B show the preparation of maize sample elements 41, to give optically thin sample elements 48. This is achieved by placing the sample elements 41 into the sample holder 46, whereas the sample holder 46 is placed onto a base plate 49. The lever consisting of a pair of blades 44,45 is fixed by the pin 42 and can be moved over the sample holder 46, whereas blade 44 moves along plane P1 and the parallel, lower blade 45 along plane P2, slicing each sample element 41 from two sides within said planes P1,P2. The sample slices 47 are disposed of and the sample holder 46 readily contains optically thin sample elements 48 of maize of about 2 to 3 millimeter of thickness. The hidden mass is then lower than approximately 20% giving a very reliable spectral result.

In an alternative embodiment the optically integrating cavity of FIGS. 2 and 3 is used to measure samples such as hay. The hay may simply be placed in the space, which is assigned to the sample holder 27. In other words, the sample holder 27 is not used, rather, the protection glasses 29,39 compress the hay to a desired thickness, which ideally can fulfill the condition for optical thinness. Even without the protection glasses 29,39 parts of plants, such as hay, may be placed uncompressed into the integrating cavity for the optical measurement.

Figure 5:
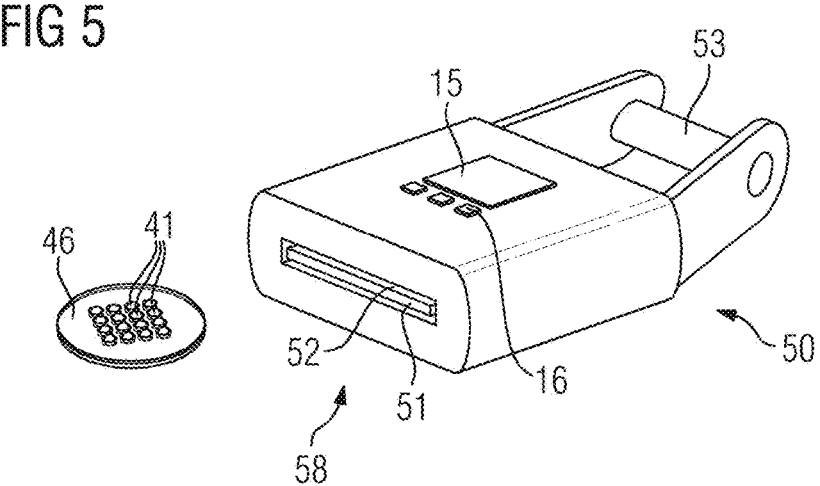
FIG. 5 shows an optical analyzer with an integrated sample preparation device.
Figure 6:
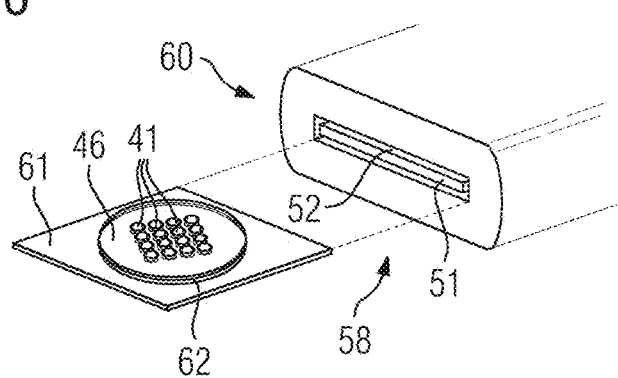
FIG. 6 shows a sample holder plate during the insertion into an optical analyzer.

FIGS. 5 and 6 show easy-to-handle portable optical analyzers 50,60 with an integrated sample preparation device. In both cases the sample elements 41 are placed onto the sample holder 46, whereas a pair of blades 51,52 slices the sample elements 41 into optically thin sample elements 48. The insertion and the slicing can be carried out in one single step, which can be performed by a single person.

The handle 53 in FIG. 5 is useful since counter force for the slicing can be generated by moving the sample holder 46 with one hand and producing the counter force onto the handle 53 until the sample holder enters the slot 58.

The optically integrating cavity is integrated inside the optical analyzers 50,60 and needs not to be opened for the measurement. Once inserted into the cavity, the sample holder 46 is advantageously surrounded by a protection glass unit (not visible) which prevents any dirt from falling onto the diffusely reflecting walls of the cavity. The protection glass unit and the blades 51,52 are advantageously integrated into a single mechanical unit that can be relatively easily removed from the enclosure of analyzers 50,60, for instance, by using a simple tool like a screwdriver. This allows periodic checking and, if necessary, cleaning of the protection glass unit as well as, if necessary, replacement of the blades 51,52.

In FIG. 6 the insertion is further aided by a sample holder plate 61, which takes care of the proper insertion and allows the use of the optical analyzers 50,60 with different sample holders 46 being utilized like adapters. The sample holder plate 61 has a receptacle 62, which is adapted to host the sample holder 46.

Figure 7:
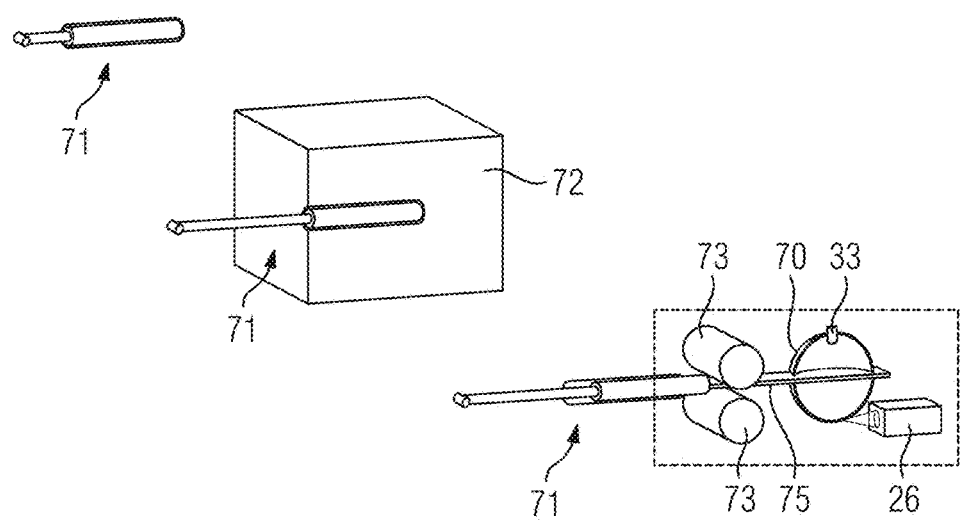
FIG. 7 shows the preparation and measurement of a sample plate of an agricultural product.

FIG. 7 shows the preparation of sample plates 75 of an agricultural product 72, such as hay. The sampler 71 is a state of the art sampler 71, which is being used to probe the agricultural product 72 by its insertion into it and filling up its probe container by mechanical action. The probed agricultural product is then pressed out of the sampler 71 and pressed (thereby flattened) down to a required thickness of hay to fulfill the optical thinness requirement for hay. This way the sample plate 75 of hay is produced by at least one pair of rollers 73.

The sample plate 75 is then introduced into an optically integrating cavity 70, such as a sphere with white diffusing walls. Due to its shape it can be used like a common transmission filter glass and can be placed between both half-spheres. Due to the homogeneous light distribution there is mainly filtered light in the sphere, ensuring a very low irradiance offset in the experiment.

The embodiment of FIGS. 5 and 6 may be altered in such a way that the pair of blades 51,52 is not necessary by not using a sample holder 46 with sample elements 41 and possibly also a sample holder plate 61, but using a sample plate 75 instead without any holders 61,46.

The invention should not be understood as being limited only to the attached claims, but should be understood as including all their legal equivalents.

REFERENCE NUMERALS USED

B operating direction
D minimal distance
P1 first plane
P2 second plane
1 detector array
2 linear variable optical bandpass filter
3 cylindrical lens
4 focusing lens
10 optical analyzer
11 half-sphere/lid
12 hinge
13 light source
14 baffle
15 display
16 button
17 sample holder 18 indentation
19 protection glass
20 optically integrating sphere
21 half-sphere
22 handle
23 slot
24 lower half-sphere
25 opening
26 spectral sensor arrangement
27 sample holder
29 protection glass
31 optical light diffusing wall
33 light source
34 baffle
36 diffused light
38 frame
39 protection glass
40 sample preparation device
41 maize sample elements
42 pin
43 handle
44 first blade
45 second blade
46 sample holder
47 sample slices
48 optically thin sample elements
49 base plate
50 optical analyzer
51 lower blade
52 upper blade
53 handle
54 indentations
58 sample slot
60 optical analyzer
61 sample holder plate
62 receptacle
70 optically integrating cavity
71 sampler
72 agricultural product
73 compression rollers
75 sample plate

The invention claimed is:

1. An optical analyzer comprising:
   an optically integrating cavity, the optically integrating cavity formed by at least one optical light diffusing wall and adapted to contain a sample of a solid agricultural product, said sample consisting of one or more sample elements;
   a light source emitting light into the optically integrating cavity, wherein the at least one optical light diffusing wall is utilized to convert emitted light to diffused light and wherein the sample at least partially or completely converts the diffused light to spectrally filtered light, the optical analyzer being configured to provide a homogeneous photon density in the integrating cavity and to provide a homogeneous illumination of the sample from all spatial directions; and
   a spectral sensor, wherein the sample is confined in the optically integrating cavity while the spectral sensor is exposed to the spectrally filtered light.

2. The optical analyzer according to claim 1, wherein the optically integrating cavity is further adapted such that the sample elements are suspended separately from each other within the optically integrating cavity.

3. The optical analyzer according to claim 2, wherein the optical analyzer is adapted to allocate the sample elements at a minimum distance (D) from each other.

4. The optical analyzer according to claim 3, wherein the sample elements are allocated by indentations of a sample holder and the optical analyzer being adapted to receive the sample holder in the optically integrating cavity.

5. The optical analyzer according to claim 4, wherein the sample holder is in part or completely transparent for the emitted light.

6. The optical analyzer according to claim 4, wherein the sample holder has between 50 to 110 indentations, each indentation adapted to position or hold the respective sample element.

7. The optical analyzer according to claim 4, wherein a thickness of the sample holder corresponds to the characteristic thickness of an optically thin sample.

8. The optical analyzer according to claim 7, wherein a blade or a pair of blades is positioned at an entrance opening of a slot to convert the sample to an optically thin sample by partial slicing of the sample elements when the sample is inserted into the optical analyzer.

9. The optical analyzer according to claim 1, wherein the optical analyzer is adapted to analyze an optically thin sample.

10. The optical analyzer according to claim 1, wherein the optical analyzer has an energy storage capable of storing an energy load sufficient for the optical analyzer to carry out a spectral analysis of the sample.

11. The optical analyzer according to claim 10, wherein the energy storage is a storage of electric energy.

12. The optical analyzer according to claim 1, wherein the optical analyzer is adapted to carry out an optical analysis of the sample while being held manually.

13. The optical analyzer according to claim 1, wherein the space between the sample elements is kept non-absorbing or nearly non-absorbing in comparison to the absorption caused by the sample elements.

14. The optical analyzer according to claim 1, wherein some or all of the sample elements are allocated in a plane, a line or a sphere.

15. The optical analyzer according to claim 1, wherein the sample is a pressed or cut sample plate of an agricultural product.

16. The optical analyzer according to claim 1, wherein a sample holder is placeable and/or is fixed inside the optically integrating cavity by means of a frame, by means of a form fit or by means of a force closure.

17. The optical analyzer according to claim 1, wherein the optical analyzer has a sample slot for inserting the sample.

18. The optical analyzer according to claim 1, wherein the solid agricultural product is a granular agricultural product.

19. The optical analyzer according to claim 18, wherein the sample is of a treated granular agricultural product.

20. The optical analyzer according to claim 1, wherein the light source is a light bulb, light emitting diode (LED), a broad bandwidth emitting diode, a halogen lamp or a multiple of said light sources.

21. The optical analyzer according to claim 1, wherein the wavelength spectrum of the light source is at least partially located in the spectral range from 800 to 1050 nanometer.

22. The optical analyzer according to claim 1, wherein the optical light diffusing wall is painted with a diffuse white paint, the optical light diffusing wall has a layer of highly diffuse material or the optical light diffusing wall is made from a diffuse material.

23. The optical analyzer according to claim 1, wherein the optically integrating cavity comprises two half-spheres.

24. The optical analyzer according to claim 23, wherein at least one of the half-spheres is sealed with a transparent protection.

25. The optical analyzer according to claim 1, wherein the spectral sensor has a detector array, a linear variable optical filter and/or focusing means.

26. The optical analyzer according to claim 1, wherein an analysis of an absorption spectrum provided by the spectral sensor results in the concentration of protein, moisture, carbohydrate and/or fat contained within the sample.

27. An optical analyzing method comprising the steps of:
emitting optical light into an optically integrating cavity, wherein at least one optical light diffusing wall of the optically integrating cavity converts emitted light to diffused light;
at least partially or completely converting the diffused light into spectrally filtered light by utilizing a sample of a solid agricultural product, the sample being confined in the optically integrating cavity while the spectral sensor is being exposed to the spectrally filtered light, a photon density in the integrating cavity being homogeneous and providing a homogeneous illumination of the sample from all spatial directions, said sample consisting of one or more sample elements; and
analyzing the spectrally filtered light by generating an absorption spectrum of the sample.

28. The optical analyzing method according to claim 27, wherein the sample elements are suspended separately from each other within the optically integrating cavity.

29. The optical analyzing method according to claim 27, wherein a quantitative analysis is carried out by generating the absorption spectrum.

30. The optical analyzing method according to claim 27, wherein a dark spectrum is generated for calibration while the light source is switched off or shuttered.

31. The optical analyzing method according to claim 27, wherein a majority of the sample elements is suspended separately from each other within the optically integrating cavity.

32. The optical analyzing method according to claim 27, wherein the sample elements are allocated in an optically integrating cavity at a minimum distance (D) from each other.

33. The optical analyzing method according to claim 27, wherein an optically thin sample is analyzed.

34. The optical analyzing method according to claim 27, wherein the spectral analysis is carried out by an optical analyzer powered by an energy storage capable of storing an energy load sufficient to carry out a spectral analysis of the sample.

35. The optical analyzing method according to claim 34, wherein the energy storage is a storage of electric energy.

* * * * *